United States Patent [19]

Marinak et al.

[11] Patent Number: 4,487,935

[45] Date of Patent: Dec. 11, 1984

[54] PRODUCTION OF MIXTURES RICH IN 6-CHLORO-2-TRICHLOROMETHYL PYRIDINE

[75] Inventors: Michael J. Marinak, Kelso; John L. Simonson, Longview, both of Wash.

[73] Assignee: Kalama Chemical, Inc., Kalama, Wash.

[21] Appl. No.: 468,283

[22] Filed: Feb. 22, 1983

Related U.S. Application Data

[63] Continuation-in-part of Ser. No. 422,754, Sep. 24, 1982, abandoned.

[51] Int. Cl.$^3$ .............................................. C07D 213/60
[52] U.S. Cl. ..................................................... 546/345
[58] Field of Search ......................................... 546/345

[56] References Cited

U.S. PATENT DOCUMENTS

| | | | |
|---|---|---|---|
| 3,135,594 | 9/1964 | Goring | 546/345 |
| 3,256,167 | 6/1966 | Norton et al. | 546/345 |
| 3,420,833 | 1/1969 | Taplin | 546/345 |
| 3,424,754 | 1/1969 | Taplin | 546/345 |
| 4,256,894 | 3/1981 | Dietsche et al. | 546/345 |

FOREIGN PATENT DOCUMENTS 957276  5/1964  United Kingdom ................ 546/345

OTHER PUBLICATIONS

Pesticide Manufacturing and Toxic Materials Control Encyclopedia (1980), pp. 559–561).
Affidavit Under Rule 131 by William H. Taplin III, dated Nov. 28, 1967, (located in file history of Taplin U.S. Pat. No. 3,424,754).
Kosorotov et al., Zhurnal Organischeskoi Khimii, vol. 16, No. 10, pp. 2163–2171, Oct. 1980 (English Translation).
William James Sell, J. Chem. Soc., vol. 87, pp. 799 et seq. (1905).

*Primary Examiner*—Henry R. Jiles
*Attorney, Agent, or Firm*—Graybeal & Cullom

[57] ABSTRACT

Preparation of high yields of mixtures rich in 6-chloro-2-trichloromethyl pyridine by maintaining a chlorine to alpha-picoline weight ratio of greater than about 8:1 when feeding alpha-picoline hydrochloride and excess chlorine to reactor means at a temperature in the range of about 170° C. to about 250° C. in the absence of a catalyst, the reactants being contained in a well mixed diluent producing essentially no hydrogen chloride by reaction with chlorine in the indicated temperature range.

5 Claims, 1 Drawing Figure

PRODUCTION OF MIXTURES RICH IN 6-CHLORO-2-TRICHLOROMETHYL PYRIDINE

CROSS REFERENCE TO RELATED APPLICATION

This application is a continuation-in-part of our co-pending U.S. application No. 422,754, filed Sept. 24, 1982, now abandoned and entitled Production of Mixtures Rich in 6-Chloro-2-Trichloromethyl Pyridine.

BACKGROUND OF THE INVENTION

1. Field of the Invention

The present invention relates to preparation of mixtures rich in 6-chloro-2-trichloromethyl pyridine by non-catalytic liquid phase chlorination of alpha-picoline hydrochloride. Compositions enriched in 6-chloro-2-trichloromethyl pyridine are useful in agricultural applications, finding unusual application in soil culture, particularly in improving agricultural soil by retarding oxidation of ammonium ions in soil thereby improving plant nutrition therein.

2. Description of the Prior Art

The utility of 6-chloro-2-trichloromethyl pyridine as an oxidation retardant in soil is known, as in Goring U.S. Pat. No. 3,135,594. In addition, mixtures rich in 6-chloro-2-trichloromethyl pyridine and containing significant amounts of 3,6-dichloro and 5,6-dichloro-2-trichloromethyl pyridine, which are produced by the process of the subject invention, are known to be useful as raw materials in the production of 2,3,5,6-tetrachloropyridine and 2,3,4,5,6-pentachloropyridine which have known uses as herbicides and pesticides, and are also useful as chemical intermediates in the preparation of other highly desirable herbicides or pesticide products such as those described in Dietsche et al U.S. Pat. No. 4,256,894.

Previous methods for preparing mixtures rich in 6-chloro-2-trichloromethyl pyridine are described in Taplin U.S. Pat. Nos. 3,420,833 and 3,424,754, as well as The Dow Chemical Company Great Britain Pat. No. 957,276. In the examples of U.S. Pat. No. 3,424,754, yields of about 75% volatiles by weight of mixtures containing about 90% 6-chloro-2-trichloromethyl pyridine by weight (giving a net yield of about 68% by weight of 6-chloro-2-trichloromethyl pyridine) are obtained by chlorinating pre-formed alpha-picoline hydrochloride fed into the vapor space above an initiator charge heated to a reaction temperature of 220° C. In this process, an essential function of the initiator charge is to react with chlorine gas sparged into the reaction and generate HCl which is combined with the alpha-picoline in another vessel to form liquid picoline hydrochloride. Chlorine to alpha-picoline hydrochloride feed ratios of from about 1.7 to about 6.0 by weight are used in the examples of U.S. Pat. No. 3,424,754. William James Sell (J. Chem. Soc. Vol. 87, pp 799 et seq., (1905)) describes the chlorination of alpha-picoline hydrochloride at about 105°–110° C. in which the alpha-picoline hydrochloride is made by direct addition of anhydrous hydrogen chloride gas to alpha-picoline. U.S. Pat. No. 3,420,833 describes the production of mixtures rich in 6-chloro-2-trichloromethyl pyridine by reaction of alpha-picoline vapor with chlorine in the vapor phase at temperatures in excess of 400° C. in the presence of an inert diluent. Such a process is necessarily quite energy intensive because all feeds and diluents must be vaporized. Johnston et al U.S. Pat. No. 3,418,323 describes a method of preparing 6-chloro-2-trichloromethyl pyridine by reacting chlorine with 2-trichloromethyl pyridine in the liquid phase at temperatures from 120° C. to 135° C. in the presence of ultraviolet light.

SUMMARY OF THE INVENTION

The present invention is an improvement over previously known processes for producing mixture rich in 6-chloro-2-trichloromethyl pyridine, and involves chlorinating preformed alpha-picoline hydrochloride at a temperature of from about 170° C. to about 250° C. in the presence of an essentially nonreactive diluent and in the absence of a catalyst, the chlorine and picoline hydrochloride being fed to the reaction at a feed ratio of chlorine to picoline of at least about 8:1 by weight and the feed rate of picoline hydrochloride being low enough so that no substantial separation of the reactor charge into an unchlorinated picoline hydrochloride lighter phase occurs. By thus appropriately controlling the reaction, overall yields of 6-chloro-2-trichloromethyl pyridine of from 85 to 97% have been obtained in the chlorination temperature range of 200° to 250° C.

The percentage of volatiles produced (as distinguished from intractable, tar-like polymeric products) is dependent on the composition of the diluent, particularly in the 200° C. to 250° C. reaction temperature range, and also on the extent of mixing of the diluent and reactants, the relative purity of the reaction mass in the sense of lack of metallic contamination, the picoline feed rate relative to the volume of the reaction mass, and the partial pressure of chlorine, which should be greater than 50% in the vapor space to aid chlorine solubility. The composition of the diluent in which the reaction is initiated and maintained is important to the efficiency of the process of the invention in terms of securing good yields of the desired volatile chlorinated alpha-picolines, specifically 6-chloro-2-trichloromethyl pyridine. The function of such a diluent in the present process is quite different from the initiator charge described in Taplin U.S. Pat. No. 3,424,754, in which earlier process the initiator charge has the function of evolving HCl when contacted with chlorine gas at the reaction temperature. In the process of the present invention the function of the diluent is to be non-competitive for the chlorine dissolved in it so that chlorination of the alpha-picoline hydrochloride is enhanced, and also to help dissipate the heat generated by the exothermic reaction of the chlorine with the alpha-picoline hydrochloride.

Examples of some compounds which generate little if any HCl when contacted non-catalytically with chlorine under the reaction conditions are: 6-chloro, 5,6-dichloro, 3,6-dichloro and 3,5,6-trichloro-2-trichloromethyl pyridine and 2,3,6-trichloro, 2,3,5,6-tetrachloro and 2,3,4,5,6-pentachloro pyridine and mixtures thereof. This list is not meant to be a complete list of all possible diluent components but is illustrative of the type that are acceptable. The diluent may be the chlorinated pyridine/picoline products and mixtures thereof from a previous reaction which meet the above criteria and are high in content of volatiles.

In practice of this invention an excess of chlorine is fed relative to that needed for the alpha-picoline hydrochloride chlorination. This excess chlorine provides additional agitation and hence better mixing, and also a higher chlorine partial pressure which increases the chlorine solubility in the reaction media. Chlorine-to-picoline ratios in excess of 8:1 are preferred which result in chlorine being the majority of the pressure component of the gas phase. If the initiator charge were as described in U.S. Pat. No. 3,424,754 it would compete for the available chlorine and result in much lower chlorine concentrations in the gas phase and hence lower chlorine concentrations in the reaction media when compared with a non-reactive diluent. At higher temperatures the weight ratio of chlorine to alpha-picoline needs to be higher in order to achieve the high yields of the desired volatile chloro-picolines. This is necessary because the chlorine is reacting more rapidly with the alpha-picoline hydrochloride as the temperature increases and therefore the dissolved chlorine must be more rapidly replaced in the reaction medium. This is accomplished by increasing the rate of chlorine addition relative to the flow rate of the alpha-picoline hydrochloride which increases the chlorine partial pressure and hence its mole fraction concentration in the liquid reaction medium. Gas solubilities tend to decrease with rising temperature, but an increase in reactor system back pressure increases the chlorine solubility.

The alpha-picoline hydrochloride feed is to be controlled relative to the reaction volume so no more than 10% by volume of lighter phase accumulates relative to the chlorinated picoline phase. Potential decomposition products can result in the hydrochloride phase at this temperature in the absence of cooling and chlorine. This is because alpha-picoline hydrochloride is unstable at reaction temperatures in excess of 135° C. Good mixing is necessary in order to achieve dispersion of chlorine and alpha-picoline hydrochloride into the diluent. Since alpha-picoline hydrochloride and the diluent are somewhat immiscible and of different densities, sufficient agitation is required to ensure good contact.

Controlling these variables results in the yield improvements of 6-chloro-2-trichloromethyl pyridine from about 68% as per Taplin U.S. Pat. No. 3,424,754 to about 92% in the same reaction temperature range of 210°–220° C.

Care must be taken to ensure metallic impurities such as iron, copper, aluminum and other Lewis Acid type metals are excluded from the reaction medium, as they will cause different reactions in the chlorination that may not be desirable.

DESCRIPTION OF THE PREFERRED EMBODIMENTS

EXAMPLE 1

Figure 1:
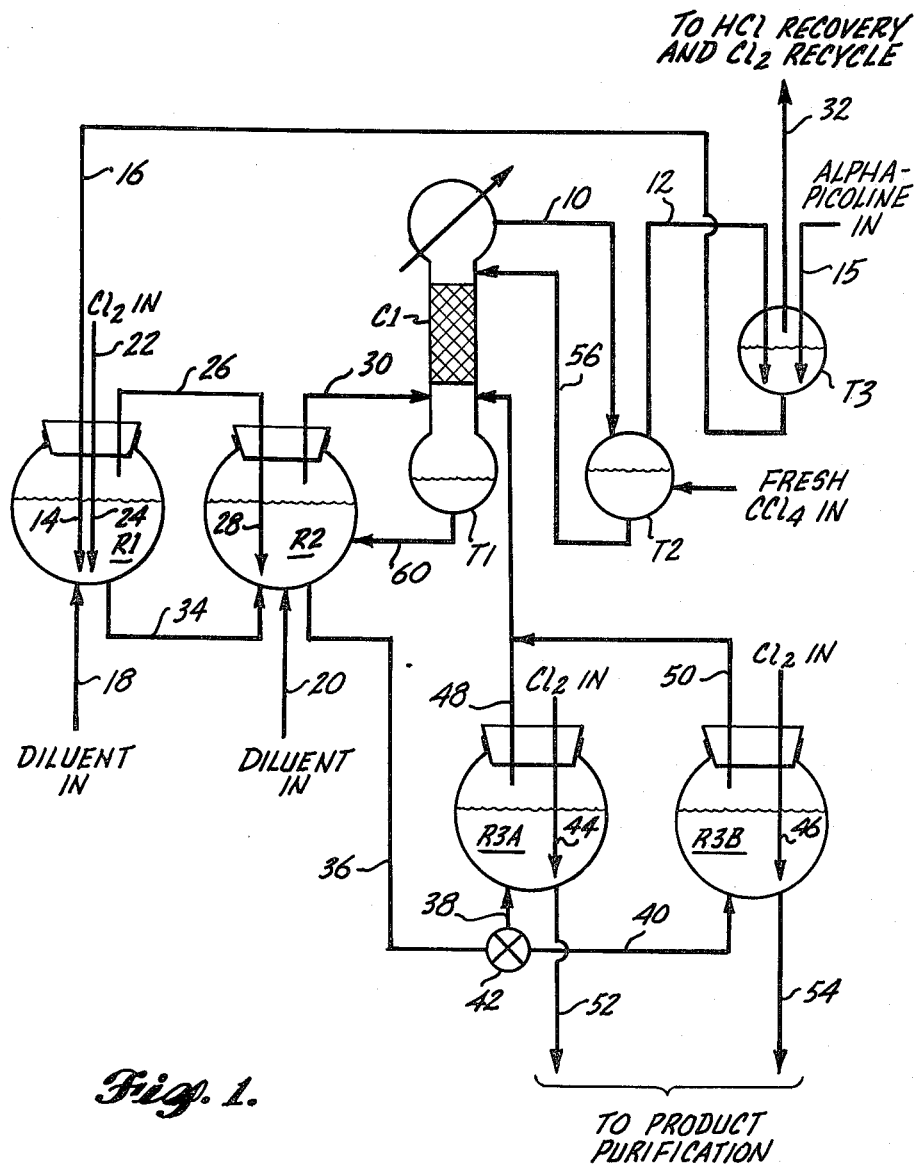
FIG. 1 is a schematic diagram of a reaction system for practicing the process of the present invention on a continuous batch basis.

FIG. 1 schematically illustrates a reaction system of a continuous batch process for producing mixtures rich in 6-chloro-2-trichloromethyl pyridine according to the present inventiion. Reactors R1, R2, R3A and R3B are glass of spherical configuration, electrically heated and each about 1 liter in volume. Water cooled quench column C1 is suitably of cylindrical design, 1½ inches in diameter, and containing as packing some 18 inches of ¼ inch glass rings.

Quench column C1 includes a holding tank or reservoir T1 and the overhead vapor from column C1 is delivered through vent line 10 to disengaging tank T2 in which the carbon tetrachloride collects, with the chlorine and hydrogen chloride evolving from column C1 being delivered by vent line 12 and sparged into hydrochlorination tank T3. For start up, alpha-picoline hydrochloride, previously prepared in a known manner as described by Sell, for example, is charged to hydrochlorination tank T3 and alpha-picoline hydrochloride is withdrawn from tank T3 and delivered to bottom discharging sparger 14 in reactor R1 through line 16. For start up, also, reactor R1 was charged with 850 grams of diluent, consisting of chlorinated alpha-picoline from a previous reaction (comprising about 96% by weight of 6-chloro-2-trichloromethyl pyridine with about 3.5% 2,3,4,5,6-pentachloropyridine), as indicated at charge line 18. 300 grams of like diluent material is also charged to reactor R2 through charge line 20. The start up sequence is that of introducing the diluent to the reactor, then initiating chlorine flow, then heating the reactor to desired reaction temperature, then initiating the alpha-picoline hydrochloride flow. By this procedure the alpha-picoline hydrochloride only sees excess chlorine in the reactor and degradation thereof to nonvolatiles is avoided. Once reactors R1 and R2 are charged, external heat is applied and the temperature thereof maintained at 210° C. Chlorine gas from a suitable source is delivered to the reactor R1 through feed line 22 and bottom placed sparger 24 at a flow rate of 440 grams per hour. The flow rate of alpha-picoline hydrochloride sparged into reactor R1 through bottom placed sparger 14, the discharge stream of which is closely adjacent to the discharge stream of chlorine sparger 24, was maintained at a rate equivalent to 22 grams alpha-picoline per hour, amounting to a chlorine to picoline feed ratio of 20:1.

As will be understood, the alpha-picoline hydrochloride fed to reactor R1 released hydrogen chloride from both the reaction with the chlorine and the decomposition of the hydrochloride salt. This hydrogen chloride along with excess chlorine is vented from reactor R1 through vent line 26 and sparged into the charge in reactor R2 through bottom placed sparger 28, the overhead vapor including hydrogen chloride and excess chlorine being vented from reactor R2 and delivered through line 30 to quench column C1, thence through line 10 and line 12 to hydrochlorinating tank T3, the vapor flow from which passes through line 32 to hydrogen chloride and chlorine gas recovery means known per se, for recyling of the chlorine gas to the process and recovery of the hydrogen chloride as desired. Once hydrogen chloride gas is being generated and passing through the system to hydrochlorinating tank T3, the alpha-picoline feed into tank T3 through line 15 can be started.

Reactor R2 is only partially charged with diluent at start up. This is for the reason that, as the volume of the reaction mass in reactor R1 increases in the course of the reaction, a portion of the reaction mass is moved from reactor R1 to reactor R2 through discharge line 34 for further chlorination in reactor R2. Then, when the volume in reactor R2 increases to the point where the reactor R2 is filled to its operating level, further increase in its volume is taken care of by progressively discharging the excess through line 36 to either reactor R3A through line 38, or to reactor R3B through line 40, depending on the setting of valve 42. Chlorination to process end point is completed in either reactor R3A or reactor R3B by continuing introduction of chlorine gas through bottom discharging spargers 44, 46, with continued heating of the reactors R3A and R3B to a preferably higher temperature than the temperature of the reaction in reactors R1 and R2, e.g. the temperature of 210° C. in the selected example. Chlorine and hydrochloride vapor take off from reactors R3A and R3B is delivered through vent lines 48, 50 to quench column C1. Chlorinated reaction product is withdrawn from the reactors R3A and R3B through respective discharge lines 52, 54, with the product going to product purification means known per se, such as a vacuum fractional distillation column. Liquid discharge from holding tank T2 is delivered to column C1 through line 56 to return carbon tetrachloride to the column C1, with make up of carbon tetrachloride from an appropriate supply if necessary, as indicated at 58. The liquid phase fraction collecting in bottom tank T1 of the quench column C1 is returned to reactor R2, as indicated at line 60.

Reactors R3A and R3B can be smaller or larger than reactors R1 and R2, depending on the desired residence time to complete the chlorination reaction. For example, with a reaction temperature of 210° C. and a residence time of 11 hours in the reactors R1 and R2, the time required to complete the reaction in reactor R3A or in reactor R3B is about 10 hours at the same temperature. The controlling factor determining reaction time in reactor R3A or reactor R3B is the concentration of 5-chloro-2-trichloromethyl pyridine in the reaction mass. This chloro-pyridine has a boiling point that is almost identical to that of 6-chloro-2-trichloromethyl pyridine and it must be completely converted to 5,6-dichloro-2-trichloromethyl pyridine, which has a higher boiling point, if a highly purified 6-chloro-2-trichloromethyl pyridine product is desired. If a purified 6-chloro-2-trichloromethyl pyridine is not necessary, then the presence of 5-chloro-2-trichloromethyl pyridine is not the controlling factor and the reaction time in reactor R3A or reactor R3B may be less.

Excess chlorine, hydrogen chloride and some volatile corrosive chloro-picoline hydrochlorides and entrained products are transferred to reactor R2 from reactor R1 by heated vent line 26 and bottom discharging sparger 28, with the volatile hydrochlorides being absorbed and reacted further in reactor R2. These hydrochlorides are very corrosive and tend to form solids on condenser surfaces that are in the 30° C. to 100° C. temperature range, the operating temperature range of quench column C1, and would there cause a plugging problem in column C1 if passed directly from reactor R1 to the column C1. Their absorption and further reaction in reactor R2 eliminate any such plugging problem since they are essentially undetectable in the vent line 30 from reactor R2. The excess chlorine, hydrogen chloride and entrained products passing to column C1 through reactor R2 vent line 30 are there scrubbed with carbon tetrachloride discharged to column C1 through line 56. The entrained chlorinated pyridine products build-up in tank T1 and the liquid level therein is controlled by recycling the excess liquid back to reactor R2 through discharge line 60.

As will be apparent, the operation of reactors R3A and R3B are in a batch manner, permitting one to be on line while the other is having the chlorinated product removed or is being filled from reactor R2. Analysis of the reaction mass in the on-line reactor R3A or R3B for residual 5-chloro-2-trichloromethyl pyridine indicates when the reaction is finished. When this occurs the contents of the on-line reactor R3A or R3B are pumped to the purification section on the system through the respective discharge line 52 or 54.

The residence time in each reactor R1, R2 and R3A or R3B varies from about 10 to about 40 hours, and the total cycle time in the reactors is about 30 to 120 hours. From the previously described feed and reaction conditions set forth in Example 1, 48 grams per hour of product that contained about 92% 6-chloro-2-trichloromethyl pyridine was produced, with the volatile content of the reaction mass being greater than 99%. In said Example 1, the other reaction products were 3,6-dichloro-2-trichloromethyl pyridine (about 1.8% by weight) and 5,6-dichloro-2-trichloromethyl pyridine (about 5.5% by weight). As known, these dichloro compounds can be separated and processed further, such as described in Dietsche et al U.S. Pat. No. 4,256,894. In this example, also, the total residence time was about 32 hours. Variation in residence time is determinable on a predictable basis, taking into consideration the product composition desired, and the reactor pressure and reactor temperature. In addition, the quantity of diluent recycled to the reactors may also be varied to vary the residence time. In any event, the feed rate of alpha-picoline hydrochloride relative to the reaction volume is to be controlled so that no greater than about 10% by volume of lighter phase (undiluted picoline hydrochloride) exists in the reaction mass.

The gases in vent line 32 from hydrochlorination tank T3 are predominantly excess chlorine and hydrogen chloride, which stream can be separated or purified by a number of conventional techniques such as absorption of the hydrogen chloride in water, or drying the chlorine and compressing the chlorine gas for recycle, or fractional distillation.

EXAMPLE 2

Utilizing the reaction system described in Example 1 and shown in FIG. 1, reactor R1 was charged with 439 grams and reactor R2 with 285 grams of the previously prepared chloro-picoline/pyridine reaction product which comprised 85% 6-chloro, 9% 5,6-dichloro, and 3% 3,6-dichloro-2-trichloromethyl pyridine. Chlorine at a rate of 580 grams per hour was sparged into reactor R1 which was heated to 170° C. The charge in reactor R2 was heated to 200° C. Alpha-picoline hydrochloride was sparged into reactor R1 for 10 hours at a rate equivalent to 22 grams per hour of alpha-picoline. Volume levels were maintained constant and equal in reactors R1 and R2. Chlorination of the reaction mass in reactor R3A at 210° C. for an additional 10 hours yield 530 grams of chlorinated picolines, which analyzed about 71% of 6-chloro-2-trichloromethyl pyridine, with about 11% 3,6-dichloro-2-trichloromethyl pyridine and about 14% 5,6-dichloro-2-trichloromethyl pyridine by weight.

EXAMPLES 3 THROUGH 8

Examples 3 through 8 serve to illustrate some of the process variables which can occur with respect to the process of the present invention, and for such purpose were conducted on a simplified, batch process basis. A chlorination reactor comprised of a 250 ml spherical glass reactor (except in Example 8 where a 1000 ml reactor was used), heated by an electric heating mantle, was equipped with two sparge tubes and a vent line to a caustic scrubber. The spargers were bottom placed and closely spaced (2 cm apart) and the respective feed lines to the spargers were fed through rotometers and flow controlled through respective needle valves, one being supplied from a source of chlorine gas and the other supplied from a source of preformed alpha-picoline hydrochloride. In each run the procedure followed was the same except for the variables investigated, namely temperature, chlorine-to-picoline feed ratio, residence time, and picoline hydrochloride flow rate relative to reaction mass volume. In Example 3, which is illustrative, the reactor was charged with 50 grams of the essentially nonreactive chloro-picoline/pyridine diluent, and chlorine feed was initiated through the chlorine sparger at a rate of 65 grams per hour and the charge heated to a temperature of 170° C. Alpha-picoline hydrochloride feed was then commenced at the rate of 5 grams alpha-picoline per hour through its sparger, with both feeds continuing for a period of 6 hours. In Example 3 the chlorine to alpha-picoline feed ratio by weight during this period was 13:1. The alpha-picoline hydrochloride feed was then stopped, the temperature raised to 200° C. and the chlorine feed was continued for an additional 15 hours at a feed rate of 65 grams per hour. The gross weight of the resulting reaction product was 129 grams, indicating a net product production of 79 grams. The processing parameters were as set forth in the following Table ONE and the constituency of the reaction product produced was as set forth in the following Table TWO. As reflected by these Tables, the product constituency in the instance of Example 3 was 50.5% 6-chloro-2-trichloromethyl pyridine, 1.9% 5-chloro-2-trichloromethyl pyridine, 18.5% 5,6-dichloro-2-trichloromethyl pyridine and 11.3% 3,6-dichloro-2-trichloromethyl pyridine, by weight, determined by gas chromatography. In the instance of Example 3, also, the volatiles present were greater than 99% by weight, as measured by internal standard gas chromatography, and the overall yield of 6-chloro-2-trichloromethyl pyridine was about 50% by weight. As indicated, additional runs, designated Examples 4, 5, 6 and 7, involved the processing parameters set forth in Table ONE and produced reaction products comprising the compounds set forth in Table TWO.

TABLE ONE

|  | Ex 3 | Ex 4 | Ex 5 | Ex 6 | Ex 7 | Ex 8 |
|---|---|---|---|---|---|---|
| Diluent charge | 50 gms | 50 gms | 50 gms | 50 gms | 50 gms | 753 gms |
| Initial Reaction Temp | 170° C. | 185° C. | 200° C. | 220° C. | 210° C. | 240° C. |
| Cl₂ Flow Rate | 65 gms/hr | 70 gms/hr | 70 gms/hr | 70 gms/hr | 70 gms/hr | 380 gms/hr |
| Alpha-Picoline hydrochloride flow rate (as -picoline) | 5 gms/hr | 4.75 gms/hr | 7 gms/hr | 5.33 gms/hr | 5 gms/hr | 8.3 gms/hr |
| Cl₂ to alpha-picoline ratio (by weight) | 13/1 | 16/1 | 10/1 | 13/1 | 14/1 | 46/1 |
| Reaction Time with both Cl₂ and picoline feeds | 6 hrs | 6 hrs | 6 hrs | 5 hrs | 5 hrs | 4 hrs |
| Additional reaction time and temp with Cl₂ feed only | 15 hrs @ 200° C. | 10 hrs @ 200° C. | 8 hrs @ 200° C. | 2 hrs @ 220° C. | 8 hrs @ 220° C. | — |
| Amt of product produced | 79 gms | 70 gms | 106 gms | 66 gms | 60 gms | 82 gms |
| Volatility of produced product | 99% | 97% | 98% | 95% | 98% | 99% |
| Yield of 6-chloro-2-trichloromethyl pyridine (by weight) | 50.5% | 60% | 85% | 92% | 86% | 97% |

In Examples 3 and 4, the composition of the diluent initially charged to the reactor 1 was 90% 6-chloro-2-trichloromethyl pyridine, 6% 5,6-dichloro-2-trichloromethyl pyridine, 2% 3,6-dichloro-2-trichloromethyl pyridine, and 1% pentachloro pyridine, by weight. In Examples 5 and 7, the diluent initially charged to the reactor was 96% 6-chloro-2-trichloromethyl pyridine, 1% 5,6-dichloro-2-trichloromethyl pyridine and 1% 3,6-dichloro-2-trichloromethyl pyridine, by weight. In Example 6 the initial charge of diluent was 85% 6-chloro-2-trichloromethyl pyridine, 9% 5,6-dichloro-2-trichloromethyl pyridine, and 3% 3,6-dichloro-2-trichloromethyl pyridine, by weight. In Example 8, the diluent initially charged to the reactor was 77% 6-chloro-2-trichloromethyl pyridine, 12% 5,6-dichloro-2-trichloromethyl pyridine, 4.5% pentachloropyridine, 2% 4,6-dichloro-2-trichloromethyl pyridine, and 1.5% 3,6-dichloro-2-trichloromethyl pyridine, by weight.

TABLE TWO

| Compound | (Ex 3) 170° C. Initial Reaction Temp | (Ex 4) 185° C. Initial Reaction Temp | (Ex 5) 200° C. Initial Reaction Temp | (Ex 6) 220° C. Initial Reaction Temp | (Ex 7) 210° C. Initial Reaction Temp | (Ex 8) 240° C. Initial Reaction Temp |
|---|---|---|---|---|---|---|
| Cl—(pyridine)—CCl₃ | 50.5% | 60.0% | 85.0% | 92.0% | 86.0% | 97.5% |
| Cl—(pyridine)—CCl₃ (isomer) | 1.9 | 8.2 | 5.5 | — | — | — |
| Cl,Cl—(pyridine)—CCl₃ | — | — | — | — | — | 2.5% |
| Cl,Cl—(pyridine)—CCl₃ | 18.5 | 8.8 | 2.8 | 1.5 | 7.0% | — |
| Cl—(pyridine)—Cl,CCl₃ | 11.3 | 6.4 | 2.4 | 1.1 | 2.0% | — |

An important variable in practice of the process of the present invention is the reaction temperature. In general, a 10° C.–15° C. temperature increase approximately doubles the rate of reaction, so there is a predictable relationship existing between reaction temperature and reaction residence time within the range of reaction temperature contemplated by the invention. In general, also, it has been determined that temperatures below about 170° C. are not practical from the point of view of realizing any substantial yield of the desired reaction products, and temperatures above 250° C. are also not practical from the same point of view in that other, more nonvolatile chlorinated reaction products are realized at higher temperatures.

The chlorination process described in Taplin U.S. Pat. No. 3,424,754 relies on chlorine gas sparging into the liquid reaction mass to dissolve the chlorine in the reaction mass and to mix the alpha-picoline hydrochloride with the initiator charge. According to Chemical Engineering Handbook, Perry, 3d Edition, page 1215 (1950), agitation produced by the degree of gas sparging involved in the process of U.S. Pat. No. 3,424,754 (estimated to be about 1.5 cubic foot per square foot minute at 200° C.) is usually too mild to move immiscible liquids with appreciable density differences into good contact with each other. In reactions as contemplated by the present invention, it is a practical necessity to maintain the reaction mass well mixed so that there is good contact and quick dispersion of the alpha-picoline hydrochloride into the diluent at the desired reaction temperatures (170° C. to 250° C.) because the polychlorinated alpha-picoline diluent and the alpha-picoline hydrochloride are immiscible and have substantially different densities (about 1.6 and about 1.2 grams per cubic centimeter, respectively), and because alpha-picoline hydrochloride is unstable in this temperature range, i.e. the salt tends to break down to its components, namely hydrogen chloride and alpha-picoline. If there is breakdown into the components, the hydrogen chloride is volatile and escapes through the vent system and alpha-picoline builds up in the lighter liquid phase. It is taught in U.S. Pat. No. 3,424,754 that feeding alpha-picoline in any substantial quantity directly into a chlorination reaction at a temperature in excess of 140° C. results in intractable mixtures of tars and polymers. Such tendency to form higher molecular weight reaction products increases at higher reaction temperatures. Mixing and chlorine feed rates of the degree described in U.S. Pat. No. 3,424,754 tend to provide poor contact between the liquid phases of the reaction mass and allow the undesirable reaction of alpha-picoline hydrochloride as discussed above to proceed. In fact, based on the analytical data presented in the examples of U.S. Pat. No. 3,424,754, at least about 25% of the alpha-picoline hydrochloride is lost in such prior art process to formation of nonvolatiles.

It has been discovered that yields of volatile chlorinated picolines in excess of 99% and other new useful products are obtained when care is taken to ensure a high partial pressure of chlorine and sufficient mixing and quick dispersion of the alpha-picoline hydrochloride into a chlorine rich diluent which does not substantially compete for the available chlorine. This is accomplished by sparging chlorine (in excess of that needed for the reaction) and alpha-picoline hydrochloride near the bottom of the polychlorinated pyridine diluent charge. The mixing required to ensure adequate contact between the liquids and gas can be achieved by high gas flow rate sparging, mechanical agitation, or a combination of both. High gas flow rates as described by Braulich, A. J.; Ch. E. Journal, Volume 11, No. 1, pp 73–79, can achieve mixing of a magnitude almost equivalent to high power input mechanical mixing. Several disadvantages are inherent in the use of high gas flow rates, however. They are:

(a) high entrainment of the reactor liquids to the quench column C1 where they are scrubbed with carbon tetrachloride and must be recycled to the reaction system.

(b) a large volume of chlorine gas which must be purified, dried, and recycled.

Another mode of operation to enhance mixing is to combine mechanical agitation with chlorine gas and alpha-picoline hydrochloride sparging to achieve the desired degree of mixing and excess chlorine. High maintenance of mechanical seals and agitators are some of the disadvantages of such a mechanical agitation system.

An increase in reactor back pressure aids in increasing the chlorine concentration in the reaction liquid. The stoichiometric amount of chlorine reacted per pound of alpha-picoline fed is greater than 3 to 1 by weight. At least a 100% excess of stoichiometric chlorine required as feed is preferred to ensure that the alpha-picoline hydrochloride does not form undesirable tars and polymers. This feed rate ensures at least a 50% molar concentration of chlorine in the vapor above the reactors. Therefore, weight ratios of at least about 8:1 of chlorine to alpha-picoline being fed are deemed necessary in practice of the present process.

Several runs were tried where the gas and liquid spargers were just under the reaction mass liquid levels. This resulted in poor mixing lower rates of reaction, and poor yields of volatiles, particularly at temperatures in excess of 200° C. Good agitation was achieved at the same chlorine gas and alpha-picoline hydrochloride flow rates per unit area, but with significantly higher liquid level depths above the sparger discharge streams. For example, at 210° C. and an 8:1 chlorine to alpha-picoline feed ratio and with a chlorine flow rate of 530 grams/hr but with the spargers just barely under liquid level resulted in 75% volatiles and a 57% yield of 6-chloro-2-trichloromethyl pyridine while a similar run with better coverage of the sparger a 98% volatile and a 86% yield of 6-chloro-2-trichloromethyl pyridine was obtained. In the lower yield example a 5 liter spherical reactor was used which had a diameter of about 8 inches and a liquid depth of about 1 inch over the sparger nozzle. In the higher yield example the liquid level over the sparger nozzle in a like reactor was about 5 inches. In both cases the sparger nozzles were separated by about 2 inches with the chlorine sparger nozzle pointed downwardly and the alpha-picoline hydrochloride sparger nozzle pointed at the chlorine sparger nozzle.

What is claimed is:

1. The process of producing high yields of mixtures rich in 6-chloro-2-trichloromethyl pyridine by liquid phase non-catalytic chlorination of alpha-picoline hydrochloride without substantial formation of intractable nonvolatiles, said process comprising:

(a) establishing in a first and second reactor means an anhydrous diluent reactor charge which is made up of chlorinated pyridine and/or picoline compounds, said diluent being essentially nonreactive with chlorine in the sense of not forming hydrogen chloride therewith under the reaction conditions to which the reactants in said first and second reactor means are subjected;

(b) while maintaining the reactor charge in said first reactor means in the liquid phase and at a temperature of about 170° C. to about 250° C., sparging both chlorine and alpha-picoline hydrochloride into the reactor charge near the bottom thereof at a chlorine-to-picoline feed ratio of at least about 8:1 by weight and at a feed rate low enough so that any separation of the reactor charge into a second, lighter phase composed of unchlorinated alpha-picoline hydrochloride is minimized and is in any event less than about 10% of the reactor charge by volume, the excess of chlorine being fed to the reactor charge relative to the amount of alpha-picoline hydrochloride being fed thereto providing enhanced agitation of the reaction mass and sufficient chlorine to ensure that the chlorine partial pressure in the vapor space over the reactor charge is greater than 50%, such reaction conditions being maintained until substantial quantities of 2-trichloromethyl pyridine and 6-chloro-2-trichloromethyl pyridine are formed;

(c) transferring excess chlorine, hydrogen chloride, and entrained products by a heated vent line and sparger from said first reactor means to said second reactor means;

(d) transferring overflow liquid from said first reactor means to said second reactor means;

(e) continuing chlorine addition and maintaining the reaction mass in the liquid phase at a temperature within the range indicated of about 170° C. to about 250° C. in said second reactor means;

(f) transferring overflow liquid from said second reactor means to a third, finishing reactor means; and (g) continuing chlorine feed and heating of the reaction mass, without further alpha-picoline hydrochloride feed, in the liquid phase at a temperature of at least about 200° C. in said third, finishing reactor means for a time sufficient to cause chlorination of substantially all 2-trichloromethyl pyridine present to form 6-chloro-2-trichloromethyl pyridine.

2. The process of claim 1, performed in a continuous batch mode and in a series of at least four reactors, with the first two reactors having essentially inert diluent charges as in step (a) of claim 1, with the reaction conditions of step (b) of claim 1 being maintained in the first reactor, the volatile hydrochlorides being absorbed and reacted further in the second reactor, and with overflow liquid from the second reactor being transferred to the third reactor or alternatively to a fourth reactor into which third reactor or fourth reactor chlorine is sparged in a batch manner to convert substantially all 5-chloro-2-trichloromethyl pyridine from the resulting reaction mass to 5,6-dichloro-2-trichloromethyl pyridine.

3. The process of claim 2, wherein the temperature in the second reactor is higher than the temperature in the first reactor and the temperature in the third and fourth reactors is higher than in the second reactor to reduce total reaction time.

4. The process of claim 1, characterized by intermixing of the chlorine and alpha-picoline hydrochloride sparged to the first reactor, such intermixing involving high gas flow sparging of the chlorine, mechanical agitation of the reaction mass, or a combination thereof.

5. The process of claim 4, characterized by a reaction product wherein the yield of volatiles is at least about 98% by weight and the yield of 6-chloro-2-trichloromethyl pyridine in relation to the alpha-picoline hydrochloride sparged to the reaction is at least about 92% by weight.

* * * * *